(12) United States Patent
Boeglin et al.

(10) Patent No.: US 6,255,482 B1
(45) Date of Patent: Jul. 3, 2001

(54) TRIPHENDIOXAZINE COMPOUNDS

(75) Inventors: Patrick Boeglin, Rixheim (FR); Bansi Lal Kaul, Biel-Benken (CH); Peter Kempter, Bad Soden (DE)

(73) Assignee: Clariant Finance (BVI) Limited, Tortola (VG)

( * ) Notice: Subject to any disclaimer, the term of this patent is extended or adjusted under 35 U.S.C. 154(b) by 0 days.

(21) Appl. No.: 09/175,139

(22) Filed: Oct. 19, 1998

(30) Foreign Application Priority Data

Oct. 24, 1997 (DE) .............................. 197 47 175

(51) Int. Cl.⁷ ................................. C07D 498/04
(52) U.S. Cl. ................ 544/74; 544/75; 544/76; 8/506; 8/657; 106/31.77
(58) Field of Search ................ 544/74, 75, 76; 8/506, 657; 106/31.77

(56) References Cited

U.S. PATENT DOCUMENTS

| | | | |
|---|---|---|---|
| 3,956,266 | 5/1976 | Mory et al. | 260/157 |
| 3,979,386 | 9/1976 | von der Crone et al. | 260/256.4 Q |
| 4,153,798 | 5/1979 | Heise et al. | 548/305 |
| 4,515,940 | 5/1985 | Berthold | 534/565 |
| 4,526,963 | * 7/1985 | Deur | 544/74 |
| 4,738,721 | 4/1988 | Baxter et al. | 106/22 |
| 4,869,989 | 9/1989 | Raue et al. | 430/106 |
| 5,539,088 | 7/1996 | Schumacher et al. | 534/633 |
| 5,565,563 | 10/1996 | Kaul et al. | 544/74 |
| 5,698,705 | 12/1997 | Alfter et al. | 548/305.4 |
| 5,786,523 | 7/1998 | Ueno et al. | 568/735 |

FOREIGN PATENT DOCUMENTS

| | | |
|---|---|---|
| 9650735 | 10/1996 | (AU) . |
| 688237 | 6/1997 | (CH) . |
| 2425594 | 12/1974 | (DE) . |
| 2451097 | 5/1975 | (DE) . |
| 2612391 | 10/1977 | (DE) . |
| 2925541 | 1/1981 | (DE) . |
| 3917602 | 12/1990 | (DE) . |
| 4442291 | 6/1995 | (DE) . |
| 0095255 | 11/1983 | (EP) . |
| 0675172 | 10/1995 | (EP) . |
| 0686673 | 12/1995 | (EP) . |
| 0738726 | 10/1996 | (EP) . |
| 2284427 | 6/1995 | (GB) . |
| WO96/32366 | 10/1996 | (WO) . |

OTHER PUBLICATIONS

Chemical Abstracts 69: 86056, 1968.*
German Search Report, 197 47 175.7 (1998).
Derwent Patent Family Report and/or Abstracts (1999).
Chemical Abstract—vol. 72, 1970, 31697Y.
Chemical Abstract—vol. 92, 1980, 215441E.
Chemical Abstract—vol. 96, 1982, 218731T.
Chem. Abstact, Reg.—Nr. 6973–93–9, 123855–79–8, 76097–86–4 (1999).
Chem. Abstract 95–23–8 and 73778–92–4 (1999).
Derwent Abstracts, Ref. 83–726920/31 zu RD—231–009–A (1999).

* cited by examiner

Primary Examiner—Richard L. Raymond
(74) Attorney, Agent, or Firm—Susan S. Jackson; Scott E. Hanf

(57) ABSTRACT

The triphendioxazine compounds of the general formula (I)

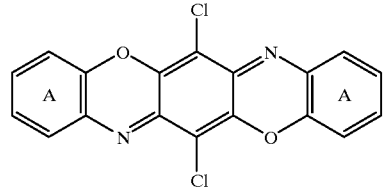

(I)

in which the rings labelled A in positions 1,2-, 2,3- or 3,4- and 8,9-, 9,10- or 10,11- carry a linearly or angularly fused heterocyclic ring containing at least one nitrogen atom which is substituted or unsubstituted, with the proviso that compounds with only unsubstituted nitrogen atoms and symmetrically disubstituted compounds with $C_{1-2}$alkyl and unsubstituted phenyl substituents are excluded,
are outstanding pigments and are notable over the closest comparable pigments in particular for better migration, light and solvent fastnesses, better heat stability and enhanced colouring power and also better dispersibility and capability to be brought into pigment form.

The invention also relates to a process for preparing these triphendioxazine compounds which is characterized by a cyclization step conducted in the presence of manganese dioxide and concentrated sulphuric acid.

3 Claims, No Drawings

TRIPHENDIOXAZINE COMPOUNDS

BACKGROUND OF THE INVENTION

GB 2284427 A describes chlorine-containing, symmetrically disubstituted triphendioxazine compounds of the following general formula

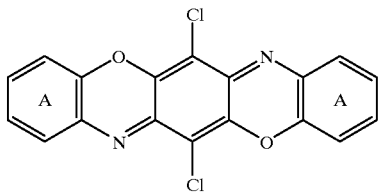

where
the rings labelled A carry rings which are fused linearly or angularly and consist of radical members, inter alia, of the formulae $-NR_1-(CO)_m-NH-$ and $-CR_1=CH-CO-NH-$ wherein $R_1$ is hydrogen, $C_{1-4}$ alkyl or phenyl, preferably hydrogen, methyl or ethyl; and m is 1 or 2.

The preparation process disclosed in GB 2284427 A starts from intermediates i.e. amino compounds, which are ortho-substituted by an alkoxy group and are obtainable only by way of a relatively complex synthesis. The pigments disclosed in GB 2284427 A are difficultly dispersible and cannot easily be brought into pigment form.

SUMMARY OF THE INVENTION

The invention relates to novel chlorine-containing triphendioxazine compounds and to their use as pigments. The invention also relates to a particularly advantageous process for preparing these triphendioxazine compounds.

It is an object of the invention to provide new pigments possessing high fastness to solvents, migration and light, which have good thermal stabilities and a high tinting power and are also easily dispersible resp. easily to be brought into pigment form.

Another object of the invention is to provide a process by which the novel pigments are obtainable and which starts from readily available intermediates.

These objects are achieved by the novel triphendioxazine compounds of the present invention and their use for preparing pigments, and by the process by which these novel triphendioxazine compounds are obtainable.

The present patent application therefore provides, firstly, compounds of the general formula (I)

DESCRIPTION OF THE PREFERRED EMBODIMENTS

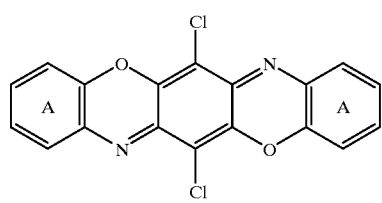

(I)

in which the rings labelled A in positions 1,2-, 2,3- or 3,4- and 8,9-, 9,10- or 10,11- carry a linearly or angularly fused heterocyclic ring containing at least one nitrogen atom which is substituted or unsubstituted, with the proviso that compounds with only unsubstituted nitrogen atoms and symmetrically disubstituted compounds with $Cl-_2$alkyl and unsubstituted phenyl substituents are excluded. Examples of such fused heterocyclic rings are enumerated in GB 2284427 which is incorporated by reference.

Preferred compounds of formula (I) are those with formulae (Ia), (IIa), (IIIa) and (IIIb)

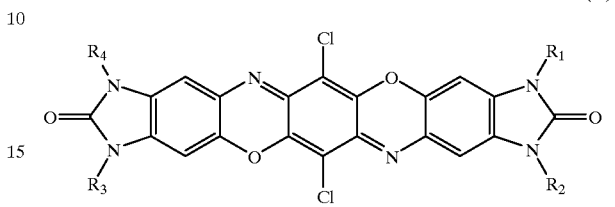

(Ia)

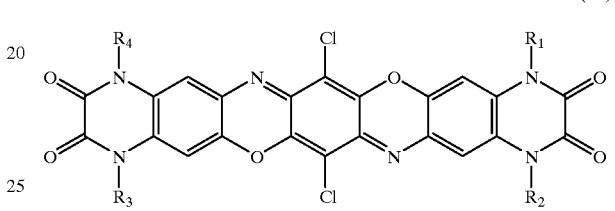

(IIa)

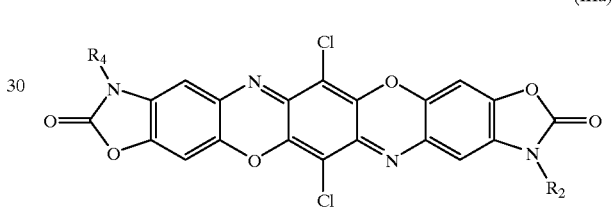

(IIIa)

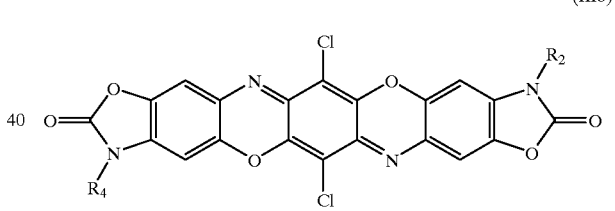

(IIIb)

where $R_1$, $R_2$, $R_3$ and $R_4$, independently of one another, are hydrogen, a $C_{1-8}$ alkyl radical, a substituted or unsubstituted phenyl, benzyl, benzanilide or naphthyl radical, a substituted or unsubstituted $C_{5-6}$ cycloalkyl radical or a radical of the formula

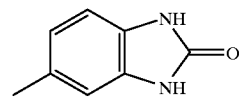

with the proviso that in the case of symmetrically disubstituted compounds the definitions hydrogen, $C_{1-2}$ alkyl radical and unsubstituted phenyl radical are excluded.

In view of the fact that only compounds having hydrogen substituents are capable of building hydrogen bridges (which is believed to be necessary for the pigmentary properties), it is surprising that even tetrasubstituted compounds possess pigmentary properties.

The substituents $R_1$, $R_2$, $R_3$ and $R_4$, independently of one another, are preferably hydrogen, a methyl radical, an ethyl radical, an n- or i-propyl radical, an n-, i-, sec- or tert-butyl radical, a cyclohexyl radical, a substituted or unsubstituted benzanilide radical, a naphthyl radical, a radical of the formula (a)

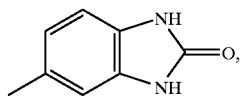
(a)

an unsubstituted phenyl radical, a phenyl radical substituted one or more times by radicals selected from the group consisting of halogen, preferably chlorine, nitro groups, phenyl radicals, $C_{1-8}$ alkyl radicals, preferably $C_{1-4}$ alkyl radicals, and $C_{1-2}$ alkoxy radicals, with the abovementioned proviso for symmetrically disubstituted compounds.

The abovementioned substituted phenyl radical in the definition of $R_1$ to $R_4$ is preferably selected from the group consisting of o-, m-, p-methyl-, ethyl-, methoxyphenyl, 2,4- and 3,5-dimethylphenyl, 2,5-dichloro-, dimethoxy-, diethoxyphenyl, m-, p-nitrophenyl, 2,5-dichloro-, 2,5-diethoxy-4-nitrophenyl, 2-methoxy-4-nitrophenyl, 3-chloro-4-methyl-, 3-chloro-4-methoxyphenyl, p-ethoxyphenyl and the radical

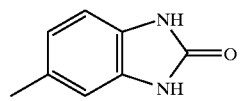
(a)

The abovementioned substituted benzanilide radical in the definition of $R_1$ to $R_4$ is preferably selected from the group consisting of radicals of the formulae (b) and (c)

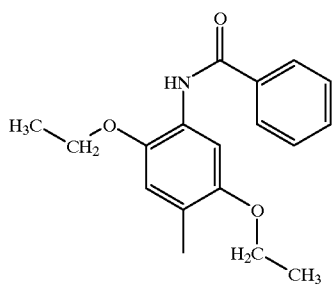
(b)

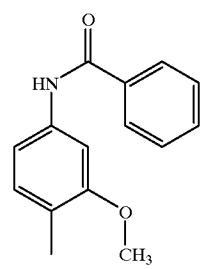
(c)

Preferred triphendioxazine compounds are those for which $R_2$ and $R_4$ are hydrogen and $R_1$ is a methyl radical and $R_3$ is an ethyl radical (asymmetrically disubstituted compound) or in which $R_1$ and $R_3$ are each a 4-methylphenyl or 4-methoxyphenyl radical (symmetrically disubstituted compounds).

Preferred symmetrically tetrasubstituted compounds are the tetramethyl-, tetraethyl-, tetrapropyl (n- or i-) and tetrabutyl (n-, i-, sec- or tert-)substituted compounds.

Preferred asymmetrically tetrasubstituted compounds are those for which the definitions of $R_1$ and $R_2$ are selected from the group consisting of the radicals methyl, ethyl, propyl (n- or i-) and butyl (n-, i-, sec- or tert-) and $R_3$ and $R_4$ can have any of the above definitions.

It has been found that even amino compounds which are not ortho-substituted are suitable as intermediates provided that the cyclization which follows the reaction with 2,3,5,6-tetra-chlorobenzoquinone (chloranil) is carried out with manganese dioxide and concentrated sulphuric acid, e.g. from 80 to 100% strength, preferably from 90 to 95% strength. The process for preparing the novel compounds of the formula (I) is therefore also an object of the present patent application. Following the reaction of 1 mol of chloranil with 2 mol of a compound of the general formula (IV)

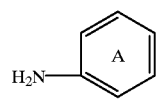
(IV)

in which ring A carries a fused heterocyclic ring containing at least one nitrogen atom which is substituted or unsubstituted with the abovementioned proviso, there follows the characterizing process step of the cyclization conducted with manganese dioxide ($MnO_2$) and concentrated sulphuric acid, e.g. from 80 to 100% strength, preferably from 90 to 95% strength.

Preferred intermediates of formula (IV) are those of formulae (XVI) to (XVIc)

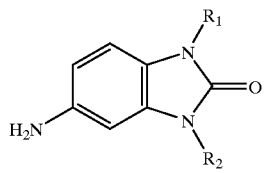
(XVI)

(XVIa)

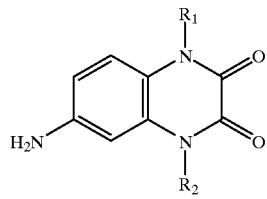
(XVIb)

(XVIc)

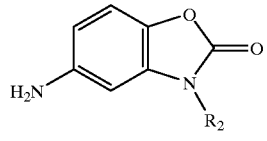

where $R_1$ and $R_2$ are as defined above.

The advantage of this process is that it is possible to start from the intermediates (XVI), (XVIa), (XVIb) and (XVIC) which, unlike the amino compounds which carry an alkoxy group in the ortho position, are relatively easy to obtain. For example, compounds of the formula (XVI) are obtainable by a process comprising the following steps:

In a first step, the reaction of 2,4-dinitrochlorobenzene (XI) with the corresponding primary amine, to give the N-substituted 2,4-dinitroaniline (XII)

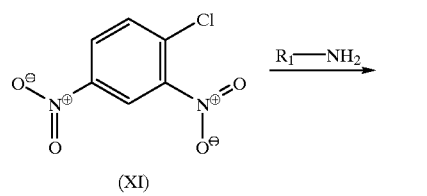

(XI)

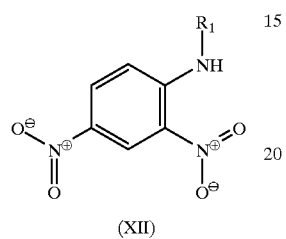

(XII)

In a second step, the reduction of the compound of the formula XII, preferably with hydrated sodium hydrogen sulphide, to give the 1,2-diamine compound (XIII)

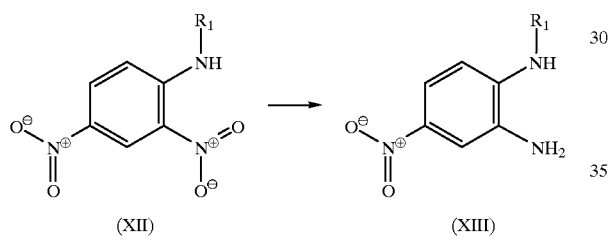

(XII)          (XIII)

In a third step, the cyclization of a compound of the formula (XIII), preferably with phosgene, chloroformic ester or urea, to give the 1,3-dihydrobenzimidazol-2-one compound

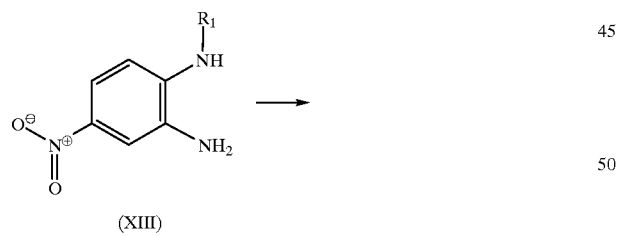

(XIII)

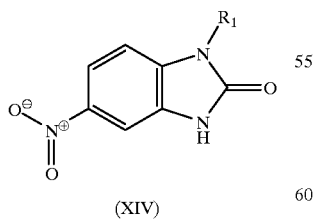

(XIV)

where $R_1$ is as defined above.

The disubstituted intermediate required to prepare the tetrasubstituted triphendioxazine compounds is obtainable, for example, by N-alkylation of the compound of the formula (XIV) in which $R_1$ is as defined above, preferably using dialkyl sulphate, alkyl bromide or alkyl iodide or, respectively, benzyl bromide or benzyl chloride, to give the compound of the formula (XV)

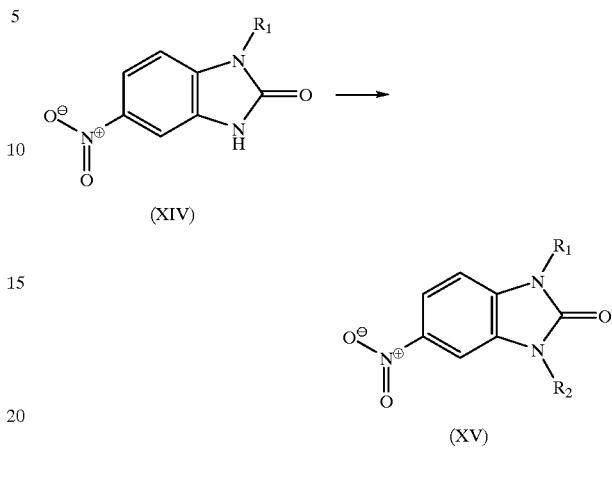

(XIV)

(XV)

In a further step, the nitro compound of the formula (XV) is reduced, preferably by the method of Bechamp, to give the amino compound of the formula (XVI)

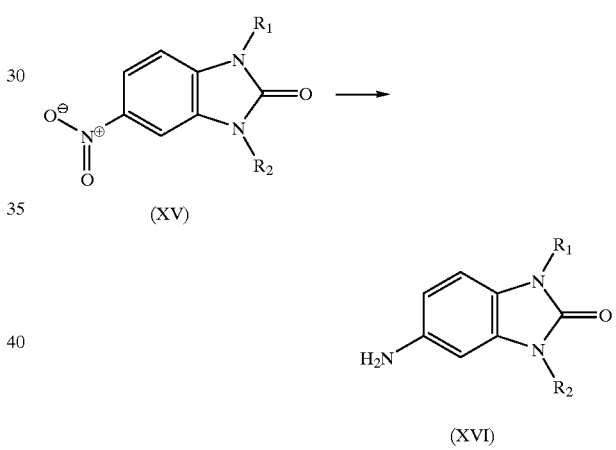

(XV)

(XVI)

where $R_1$ and $R_2$ are as defined above.

Compounds of the formula (XVIa) are obtainable, for example, by cyclizing the compound of the formula (XIII) with oxalic acid or oxalic ester.

Compounds of the formula (XVIb) (5-aminobenzoxazolones) are preferably prepared by a process comprising the following steps:

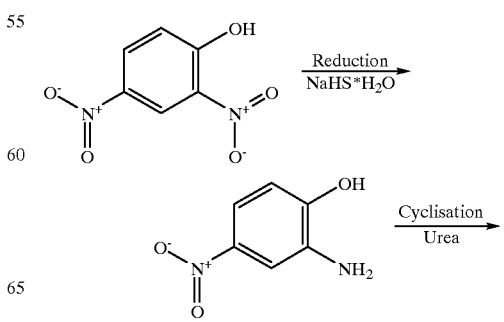

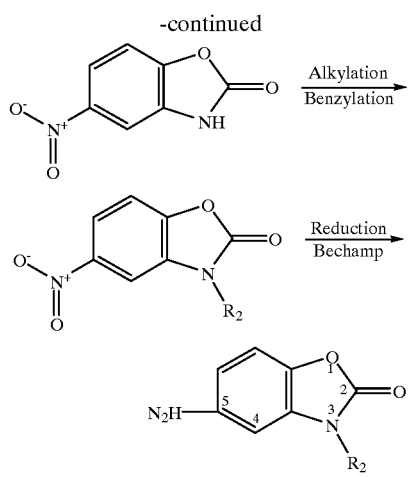

Compounds of the formula (XVIc) (6-aminobenzoxazolones) are obtainable, for example, by a process comprising the following steps:

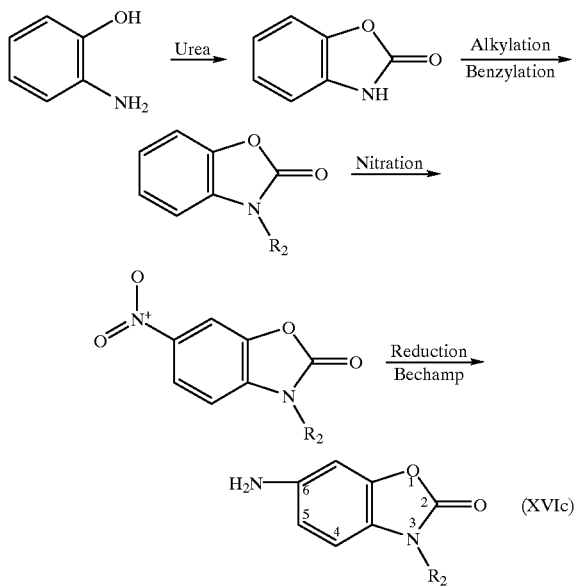

Compounds with angularly fused rings can be produced by similar methods using starting compounds having isomeric substitution, e.g. 3,4-dinitroanili ne instead of 2,4-dinitroaniline.

Triphendioxazine compounds of the formula (I) according to the invention are used as pigments.

Aftertreating the crude pigments in organic solvents in which the pigments themselves are not dissolved and at elevated temperatures, for example at from 60 to 200° C., especially from 70 to 150° C. and preferably from 75 to 100° C., can often be used to further improve the pigment properties. Aftertreatment is preferably combined with a milling or kneading operation.

The pigments according to the invention are excellently suited to the colouring of polymer compositions, by which are meant solvent-free and solvent-containing compositions comprising plastics or synthetic resins (in oil-based or water-based paints, in coating materials of various kinds, for the spin dyeing of viscose or cellulose acetate, or for pigmenting plastics, such as polyamide, polyethylene, polystyrene, polyvinyl chloride, rubber and artificial leather). They can also be used in printing inks for the graphical industry, for the colouring of paper pulps, for the coating of textile or for pigment printing.

The resulting colorations are notable for their outstanding heat, light and weather fastness, chemical resistance, colour strength and very good applications properties, examples being their crystallization fastness and dispersing fastness, and especially for their fastness to migration, bleeding, overcoating and solvents.

In addition, the pigments of the invention are also suitable as colorants in electrophotographic toners and developers, such as one- or two-component powder toners (also known as one- or two-component developers), magnetic toners, liquid toners, polymerization toners and further speciality toners (literature: L. B. Schein, "Electrophotography and Development Physics"; Springer Series in Electrophysics 14, Springer Verlag, 2nd edition, 1992).

Typical toner binders are addition polymerization, polyaddition and polycondensation resins, such as styrene, styrene-acrylate, styrene-butadiene, acrylate, polyester and phenolic-epoxy resins, polysulphones, polyurethanes, individually or in combination, and also polyethylene and polypropylene, in or to which further ingredients, such as charge control agents, waxes or flow assistants may be present or may be added subsequently.

A further area of application of pigments of the invention is their use as colorants in powders and powder coating materials, especially triboelectrically or electrokinetically sprayed powder coating materials, which are used to coat the surfaces of articles made, for example, from metal, wood, plastic, glass, ceramic, concrete, textile material, paper or rubber (J. F. Hughes, "Electrostatics Powder Coating", Research Studies Press, John Wiley & Sons, 1984).

Powder coating resins employed are typically epoxy resins, carboxyl- and hydroxyl-containing polyester resins, polyurethane resins and acrylic resins, together with customary hardeners. Combinations of resins are also used. For example, epoxy resins are frequently employed in combination with carboxyl- and hydroxyl-containing polyester resins. Examples of typical hardener components (depending on the resin system) are acid anhydrides, imidazoles and dicyandiamide and derivatives thereof, blocked isocyanates, bisacylurethanes, phenolic and melamine resins, triglycidyl isocyanurates, oxazolines and dicarboxylic acids.

The pigments of the invention are suitable, moreover, as colorants in ink-jet inks, both aqueous and non-aqueous, and in those inks which operate in accordance with the hot-melt process.

In the following examples the parts and percentages are by weight. The temperatures are indicated in degrees Celsius. One part by volume corresponds to the volume of one part by weight of water.

EXAMPLE 1

Derivatives of 1-p-tolyl-1,3-dihydrobenzimidazol-2-one a) 2,4-dinitrophenyl-p-tolylamine 310 parts of 2,4-dinitrochlorobenzene (98%) are suspended in 1250 parts of ethanol and the suspension is heated to 50° C. 325 parts of para-toluidine are added over 1.5 hours. The mixture is heated under reflux for 2 hours and filtered while hot, and the solid product is washed with 400 parts of hot alcohol. It is then washed with water until free from chloride. Drying under reduced pressure at 80° C. gives 406 parts of red-orange needles of a compound of the following formula

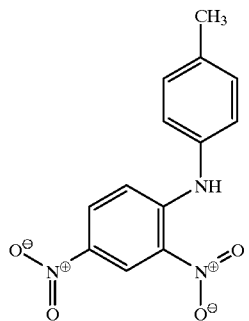

Yield: 99%

Melting point: 133.6° C.

IR (KBr): 3313–1622–1609–1581–1519–1335 cm$^{-1}$

MS(m/e):
273–256–229–226–210–196–180–168–152–139–127 b) 4-nitro-N-1-p-tolyl-1,2-diaminobenzene 382 parts of 2,4-dinitrophenyl-p-tolylamine are suspended in 1600 parts of ethanol and the suspension is heated to 55° C. A solution of 162 parts of sodium hydrogen sulphide hydrate in 300 parts of water is added dropwise over 2 hours. The mixture is subsequently stirred under reflux for 2 hours and then cooled to room temperature and filtered, and the filter cake is washed with 600 parts of alcohol and 3000 parts of water. Drying under reduced pressure at 80° C. gives 284 parts of dark red crystals of a compound of the following formula

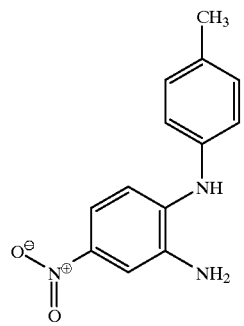

Yield: 83%

Melting point: 156.2° C.

IR (KBr): 3428–1587–1549–1478–1284 cm$^{-1}$ $^1$H-NMR (DMSO): δ: 2.25 (s, CH$_3$)–5.37 (s, NH$_2$)–6.93 (d, $^3$J=9 Hz, H—C6)–7.05 (d, $^3$J=9 Hz, 2H-C$_{tolyl}$)–7.15 (d, $^3$J=9 HZ, 2H-C$_{tolyl}$)–7.42 (dd, $^3$J=9 Hz, $^4$J=2 Hz, H—C5)–7.55 (d, $^4$J=2 Hz, H—C3)–7.70 (s, NH)

MS (m/e): 243–228–213–196–182–168–154–142–130 c) 5-nitro-1-p-tolyl-1,3-dihydrobenzimidazol-2-one 221 parts of 4-nitro-N-1-p-tolyl-1,2-diaminobenzene and 72 parts of urea are heated with stirring at 165° C. in 780 parts of o-dichlorobenzene for 4.5 hours. The mixture is subsequently cooled to room temperature and filtered and the solid product is washed with 400 parts of o-dichlorobenzene, 400 parts of methanol and 1000 parts of water. Drying under reduced pressure at 80° C. gives 234 parts of beige crystals as a compound of the following formula

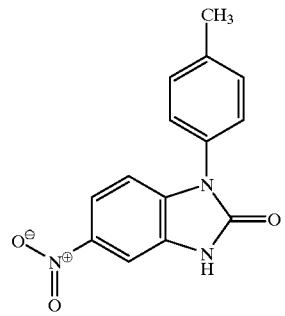

Yield: 97%

Melting point: >300° C.

IR (KBr): 3033–1725–1518–1488–1392–1343 cm$^{-1}$ $^1$H-NMR (DMSO): δ: 2.40 (s, CH$_3$)–7.06 (d, $^3$J=9 Hz, H—C7)–7.38 (d, $^3$J=9 Hz, 2H-C$_{tolyl}$)–7.41 (d, $^3$J=9 Hz, 2H—C$_{tolyl}$)–7.83 (d, $^4$J=2 Hz, H—-C4)–7.95 (dd, $^3$J=9 Hz, $^4$J=2 Hz, H—C6)–11.50 (s, H—N3)

d) 5-amino-1-p-tolyl-1,3-dihydrobenzimidazol-2-one 84 parts of iron dust and 14 parts of hydrochloric acid (36%) are heated under reflux in 700 parts of water for 1 hour. 64 parts of 5-nitro-1-p-tolyl-1,3-dihydrobenzimidazol-2-one are added over 7 hours and the mixture is subsequently stirred at this temperature for 15 hours. The mixture is then rendered alkaline with 53 parts of aqueous sodium hydroxide solution (30%), filtered to remove iron oxide, and subsequently washed with 200 parts of boiling water. Hydrochloric acid is added to adjust the filtrate to a pH of 6.5, and this filtrate is then cooled under nitrogen. The precipitated product is filtered and dried under reduced pressure at 120° C. This gives 24 parts of a pink powder of a compound of the following formula Yield: 43%

Melting point: 245–246° C.

IR (KBr): 3359–3134–1690–1637–1610–1519–1480–1396 cm$^{-1}$ $^1$H-NMR (DMSO): δ: 2.34 (s, CH$_3$)–4.84 (s, NH$_2$)–6.24 (dd, $^3$J=9 Hz, $^4$J=2 Hz, H—C6)–6.46 (d, $^4$J=2 Hz, H—C4)–6.67 (d, $^3$J=9 Hz, H—C7)–7.30 (d, $^3$J=9 Hz, H—C2', H—C6')–7.35 (d, $^3$J=9 Hz, H—C3', H—C5') –10.68 (s, H-N3)

MS (m/e): 239–210–196–182–168–148–121 e) 2,5-dichloro-3,6-bis(1-p-tolyl-2-oxo-1,3-dihydrobenzimidazol-5-ylamino)[1,4]benzoquinone 7.4 parts of sodium acetate and 21.5 parts of 5-amino-1-p-tolyl-1,3-dihydrobenzimidazol-2-one are suspended in 160 parts of ethanol and the suspension is heated to 60° C. 11.2 parts of chloranil are added over 3 hours and the mixture is subsequently refluxed for 1 hour. The solid product is filtered off hot and washed first with 400 parts of boiling ethanol and then with 300 parts of boiling water. After drying, the product is suspended in 250 parts of dimethylformamide, the suspension is heated at 90° C. for 5 hours and filtered while hot, and the solid product is washed first with 500 parts of hot (100° C.) dimethylformamide and then with 300 parts of water. Drying under reduced pressure at 80° C. gives 20 parts of a brown powder of a compound of the following formula

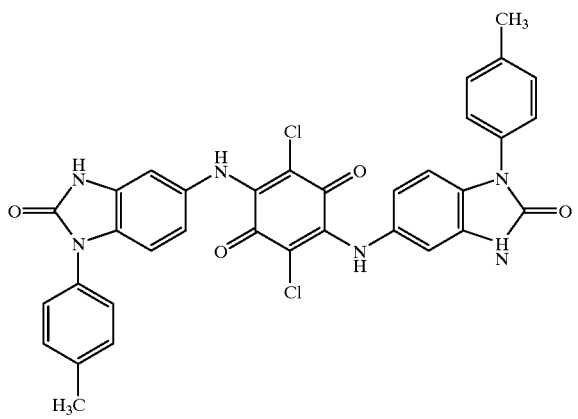

Yield: 69%

Melting point: >300° C.

IR (KBr): 3100 (1)–1696–1587–1491–1385 $cm^{-1}$ $^{1}$H-NMR (DMSO): δ: 2.40 (s, $CH_3$)–6.83 (d, $^{3}J=9$ Hz, H—C6 or H—C7)–6.89 (d, $^{3}J=9$ Hz, H—C6 or H—C7)–6.91 (s, H—C4)–7.30 (d, $^{3}J=9$ Hz, $2H_{tolyl}$) –7.41 (d, $^{3}J=9$ Hz, $2H_{tolyl}$)–9.64 (s, NH)–11.17 (s, NHCO)

f) Diimidazolone(4,5-b:4',5'-m)triphendioxazine-3,11-di-p-tolyl-6,14-dichloro-2,10-dione 180 parts of sulphuric acid (92%) are cooled to 5° C. and 17 parts of 2,5-dichloro-3,6-bis(1-p-tolyl-2-oxo-1,3-dihydro- benzimidazol-5-ylamino)-[1,4]-benzoquinone are added over 30 minutes. Then 6.1 parts of activated manganese dioxide (88%) are added over 3 hours and the mixture is subsequently heated at room temperature for 12 hours. The mixture is diluted to 80% by adding 27 parts of water, with cooling. The excess manganese dioxide is destroyed using 1.2 parts of hydrogen peroxide (30%). The product is filtered off on a polypropylene filter, washed first with 250 parts of sulphuric acid (80%) and then 250 parts of sulphuric acid (50%), and subsequently washed free from sulphate with water. Drying under reduced pressure at 80° C. gives 12.9 parts of a metallic-green powder of a compound of the following formula

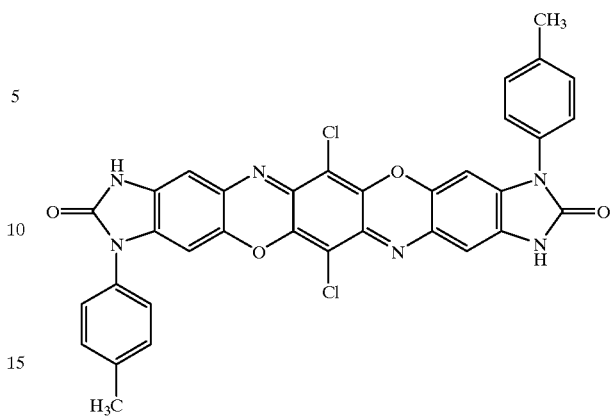

Yield: 77%

Melting point: >300° C.

IR (KBr): 3019 (1)–1712–1647–1562–1480–1309–1263 $cm^{-1}$

Microanalysis:

calc. $C_{63.07}$ H 3.11 N 12.98 Cl 10.95 O 9.88 exp. $C_{62.6}$ H 3.2 N 13.0 Cl 11.2 O 10.0

Using the method described in Example 1 further derivatives of similar 1,3-dihydro-benzimidazol-2-ones can be prepared as illustrated in Examples 2 and 3.

EXAMPLE 2

Derivatives of 1-(4-methoxyphenyl)-1,3-dihydrobenzimidazol-2-one a) 2,4-dinitrophenyl-(4-methoxyphenyl)amine b) N-1-(4-methoxyphenyl)-4-nitro-1,2-diaminobenzene c) 1-(4-methoxyphenyl)-5-nitro-1,3-dihydrobenzimidazol-2-one d) 5-amino-i-(4-methoxyphenyl-1,3-dihydrobenzimidazol-2-one e) 2,5-dichloro-3,6-bis(4-methoxyphenyl-2-oxo-1,3-dihydrobenzimidazol-5-ylamino)[1,4]benzoquinone f) Diimidazolone(4,5-b:4',5'-m)triphendioxazine-3,11-di(4-methoxyphenyl)-6,14-dichloro-2,10-dione of the following formula

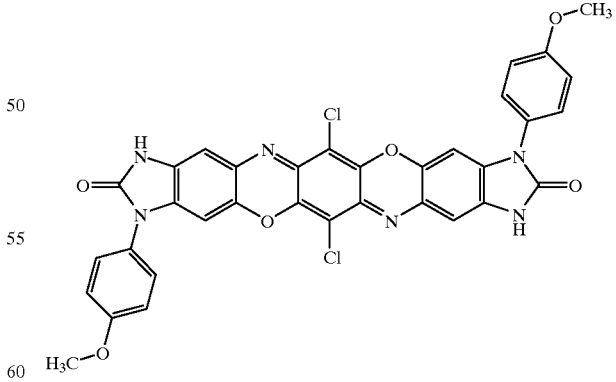

Yield: 70%

Melting point: >300° C.

IR (KBr): 3437 (1)–1702–1515–1479–1313–1257 cm$^{-1}$ $^1$H-NMR (DMSO+NaOD): δ: 2.76 and 2,92 (s, CH$_3$) –6.87 (s, H—Car)–7.01 and 7.36 (d, $^3$J=9 Hz, 2H-C$_{PhoMe}$)–7.03 (s, H—Car)–7.05 and 7.38 (d, $^3$J=9 Hz, 2H-C$_{PhoMe}$)

EXAMPLE 3

Derivatives of 1,3-dimethyl-1,3-dihydrobenzimidazol-2-one a) 1,3-dimethyl-5-nitro-1,3-dihydrobenzimidazol-2-one 90 parts of 5-nitro-1,3-dihydrobenzimidazol-2-one are suspended in 500 parts of aqueous sodium hydroxide solution (30%) and the suspension is heated to 53° C.; 161 parts of dimethyl sulphate are added dropwise over 12 hours during which the temperature rises to 70° C. The mixture is cooled to room temperature and filtered and the solid product is washed to neutrality. Drying under reduced pressure at 80° C. gives 99 parts of a beige powder of a compound of the following formula

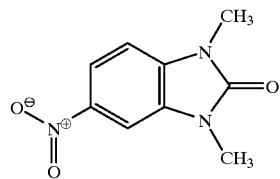

Yield: 96%

Melting point: 206.3° C.

$^1$H-NMR (DMSO): δ: 3.35 (s, CH$_3$)–3.37 (s,CH$_3$)–7.28 (d, $^3$J=9 Hz, H—C7)–7.98 (d, $^4$J=2 Hz, H—C4)–8.00 (dd, $^3$J=9 Hz, $^4$J=2Hz, H—C6)

b) 5-amino-1,3-dimethyl-1,3-dihydrobenzimidazol-2-one c) 2,5-dichloro-3,6-bis(1,3-dimethyl-2-oxo-1,3-dihydrobenzinmidazol-5-ylamino)[1,4]benzoquinone d) Diimidazolone(4,5-b:4',5'-m)triphendioxazine-1,3,9,11-tetramethyl-6,14-dichloro-2,10-dione of the following formula

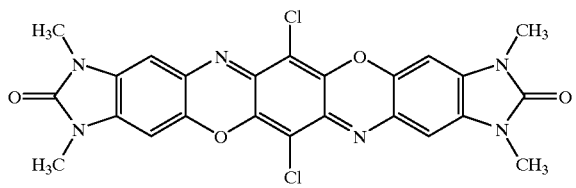

Yield: 41%

Melting point: >300° C.

Microanalysis:
  calc. C$_{55.08}$ H 3.08 Cl 13.55 N 16.06 O 12.23
  exp. C$_{54.9}$ H 3.3 Cl 13.3 N 16.1 O 12.4

EXAMPLE 4

Asymmetric Derivatives a) 2,5-dichloro-3-(1-ethyl-2-oxo-1,3-dihydrobenzimidazol-5-ylamino)-6-(1-methyl-2-oxo-1,3-dihydrobenzimidazol-5-ylamino)[1,4]benzoquinone 12 parts of sodium acetate and 15 parts of chloranil are suspended in 200 parts of ethanol and the suspension is heated to 53° C. 10.6 parts of 5-amino-1-ethyl-1,3-dihydrobenzimidazol-2-one are added over 1 hour and the mixture is subsequently heated under reflux for 1 hour. Then a further 12 parts of sodium acetate are added, followed by 9.8 parts of 5-amino-1-methyl-1,3-dihydro- benzimidazol-2-one. The mixture is stirred under reflux for 10 hours, then the solid product is filtered off hot and washed with 400 parts of boiling ethanol and then with 500 parts of boiling water. After drying, 24 parts of the product are suspended in 200 parts of dimethylformamide, the suspension is heated at 100° C. for 4 hours and filtered while hot, and the solid product is washed with 600 parts of hot (100° C.) dimethylformamide followed by 500 parts of water. Drying under reduced pressure at 80° C. gives 16 parts of a brown powder of a compound of the following formula

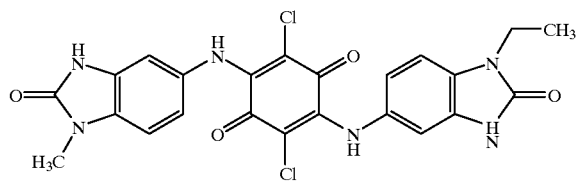

Yield: 53%

Melting point: >300° C.

IR(KBr): 3250–2978–1703–1595–1574–1501–1485 cm$^{-1}$ $^1$H-NMR (DMSO 120° C.): δ: 1.21 (t, $^3$J=6 Hz, CH$_3$) –3.31 (s, NCH$_3$)–3.83 (q, $^3$J=6 Hz, NCH$_2$)–6.84 (m, $^3$J=9 Hz, $^4$J=2 Hz, H—C4, H—C4', H—C6, H—C6') –7.03 (d, $^3$J=9 Hz, H—C7)–7.09 (d, $^3$J=9 Hz, H—C7') –9.61 (s, H—N5, H—N5')–10.86 (s, H—N3)–10.88 (s, H-N3')

b) Diimidazolone(4,5-b:4',5'-m)triphendioxazine-3-ethyl-11-methyl-6,14-dichloro-2,10-dione 150 parts of sulphuric acid (92%) are cooled to 5° C., and 15.4 parts of 2,5-dichloro-3-(1-ethyl-2-oxo-1,3-dihydrobenzimidazol-5-ylamino)-6(1-methyl-2-oxo-1,3-dihydrobenzimidazol-5-ylamino)-[1,4]-benzoquinone are added over 30 minutes. Then 7.1 parts of activated manganese dioxide (88%) are added over 3 hours and the mixture is subsequently heated at room temperature for 18 hours. The mixture is diluted to 80% by adding 22 parts of water, with cooling. The excess manganese dioxide is destroyed using 1.4 parts of hydrogen peroxide (30%). The mixture is filtered over a polypropylene filter and the solid product is washed with 250 parts of sulphuric acid (80%), then with 250 parts of sulphuric acid (50%) and subsequently is washed free from sulphate with water. Drying under reduced pressure at 80° C. gives 10 parts of metallic-green powder of a compound of the following formula

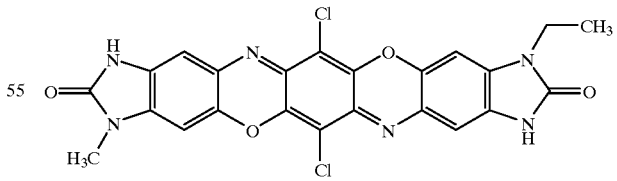

Yield: 66%

Melting point: >300° C.

IR (KBr): 3086–3000–1698–1646–1560–1485–1321 cm$^{-1}$

Microanalysis:
  calc C$_{54.22}$ H 2.75 O 12.57
  exp. C$_{54.0}$ H 2.9 O 12.7

USE EXAMPLE 1

4 parts of the pigment set out in the table below are milled in a ball mill with
96 parts of a mixture of
50 parts of a 60 per cent strength solution of coco-aldehyde-melamine resin solution in butanol,
10 parts of xylene and
10 parts of ethylene glycol monoethyl ether for 24 hours.

The resulting dispersion is sprayed onto sheet aluminium, left to dry in air for 30 minutes and then baked at 120° C. for 30 minutes. The result is a film of the colour specified in the table below, with very good migration fastness and also good light and weathering stability.

USE EXAMPLE 2

Example of the preparation of a 0.1% coloured PVC film (blend of colour pigment to white pigment 1:5):
16.5 parts of a plasticizer mixture consisting of equal parts of dioctyl phthalate and dibutyl phthalate are mixed with
0.05 parts of the pigment set out in the table below and with
0.25 parts of titanium dioxide. Then
33.5 parts of polyvinyl chloride are added.

The mixture is friction-rolled on a double-roll mill for 10 minutes, the resulting sheet being continually cut with a spatula and rolled together. In the roll mill, one roll is held at a temperature of 40° and the other at a temperature of 140°. The mixture is subsequently taken off in sheet form and pressed between two polished metal plates at 160° for 5 minutes. This gives a coloured PVC film of high brightness and very good migration and light fastness.

TABLE

| Pigment of Example | Colour in Use Example 1 | Colour in Use Example 2 |
|---|---|---|
| 1 f | violet | violet |
| 2 f | violet | violet |
| 3 d | red-violet | red-violet |
| 4 b | violet | violet |

What is claimed is:

1. A process for preparing a triphendioxazine compound of formula (I)

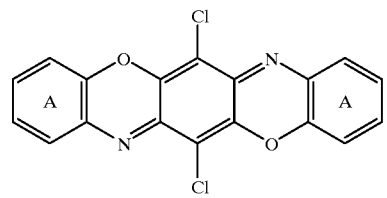

(I)

in which the rings labeled A in positions 1,2-, 2,3- or 3,4- and 8,9-, 9,10- or 10,11- carry a linearly or angularly fused heterocyclic ring containing at least one nitrogen atom which is substituted or unsubstituted, provided that compounds with only unsubstituted nitrogen atoms and symmetrically disubstituted compounds with $C_{1-2}$alkyl and unsubstituted phenyl substituents are excluded, said process comprising:

following reacting two moles of a compound the formula (IV)

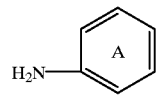

(IV)

in which ring A carries a fused heterocyclic ring containing at least one nitrogen atom which is substituted or unsubstituted, provided that compounds with only unsubstituted nitrogen atoms and symmetrically disubstituted compounds with $C_{1-2}$alkyl and unsubstituted phenyl substituents are excluded, with one mole of 2, 3, 5, 6-tetrachloro-1,4-benzoquinone (chloranil)

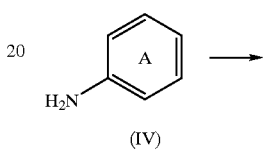

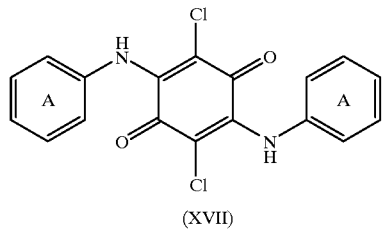

(XVII)

where the rings labeled A are as defined above, conducting the cyclization of the compound of the formula (XVII) to the compound of the formula (I)

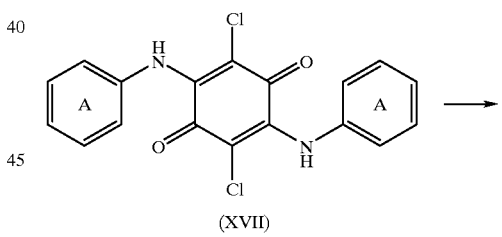

(XVII)

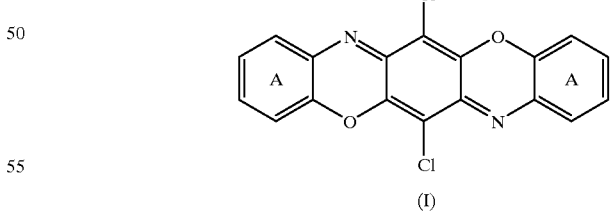

(I)

in the presence of manganese dioxide and concentrated sulphuric acid.

2. A method of coloring a material wherein the material is polymer composition, paper pulp, an electrophotographic toner or developer, a powder or powder coating, an inkjet ink, a coating, a textile, or a printing ink, the method comprising adding a triphendioxazine compound of the formula (Ia)

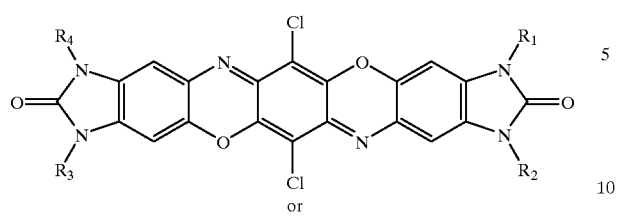

or (IIa)

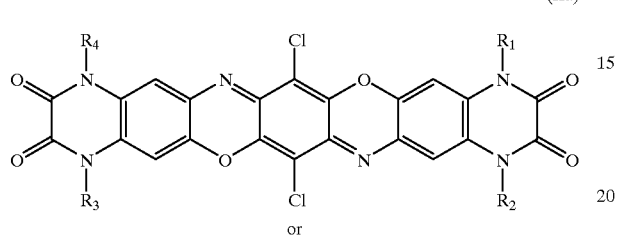

or (IIIa)

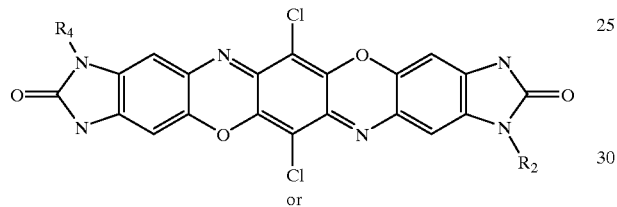

or

-continued (IIIb)

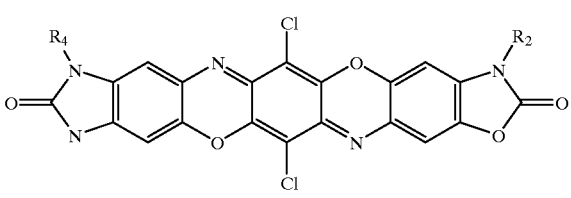

wherein $R_1$, $R_2$, $R_3$ and $R_4$, independently of one another, are hydrogen, a $C_{1-8}$ alkyl radical, a substituted or unsubstituted phenyl, benzyl, benzanilide or naphthyl radical, a substituted or unsubstituted $C_{5-6}$ cycloalkyl radical or a radical of formula (a)

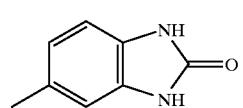

provided that in a symmetrically disubstituted compound the definitions hydrogen, $C_{1-2}$alkyl radical or unsubstituted phenyl radical are excluded, to the material.

3. The method of using according to claim 2, wherein the colorant is a pigment.

* * * * *